United States Patent [19]

Angrick et al.

[11] Patent Number: 4,656,053
[45] Date of Patent: * Apr. 7, 1987

[54] METHOD FOR PRODUCING ORTHODONTIC DEVICES AND APPLIANCES

[75] Inventors: Michael Angrick, Berlin; Ullrich Trautwein; Kurt Lenz, both of Wehrheim, all of Fed. Rep. of Germany

[73] Assignee: Kulzer & Co. GmbH, Wehrheim, Fed. Rep. of Germany

[*] Notice: The portion of the term of this patent subsequent to Feb. 4, 2003 has been disclaimed.

[21] Appl. No.: 777,835

[22] Filed: Sep. 19, 1985

Related U.S. Application Data

[63] Continuation-in-part of Ser. No. 697,776, Feb. 4, 1985, Pat. No. 4,568,558.

[30] Foreign Application Priority Data

Feb. 11, 1984 [DE] Fed. Rep. of Germany ....... 3404904

[51] Int. Cl.⁴ ............................ B05D 3/06; A01N 1/02
[52] U.S. Cl. ........................................ 427/53.1; 427/2; 427/54.1
[58] Field of Search ................ 427/53.1, 254.1, 389.9, 427/353.6, 385.5, 403, 412, 417.1, 407.1

[56] References Cited

U.S. PATENT DOCUMENTS

| | | | |
|---|---|---|---|
| 4,105,025 | 8/1978 | Wang et al. | 128/90 |
| 4,131,114 | 12/1978 | Kirkpatrick et al. | 128/90 |
| 4,238,522 | 12/1980 | Potts | 427/2 |
| 4,291,087 | 9/1981 | Warburton et al. | 427/54.1 X |
| 4,300,968 | 11/1981 | Föttinger et al. | 427/54.1 X |
| 4,316,457 | 2/1982 | Liegeois | 128/156 |
| 4,340,453 | 7/1982 | Noomen | 204/159.15 |
| 4,348,427 | 9/1982 | Priola et al. | 427/44 |
| 4,393,187 | 7/1983 | Boba et al. | 427/54.1 |
| 4,411,931 | 10/1983 | Duong | 427/54.1 |
| 4,439,480 | 3/1984 | Sachs et al. | 427/54.1 X |
| 4,568,558 | 2/1986 | Angrick et al. | 427/2 |

*Primary Examiner*—Thurman K. Page
*Attorney, Agent, or Firm*—Frishauf, Holtz, Goodman & Woodward

[57] ABSTRACT

A method for producing orthodontic devices and appliances having a highly accurate fit by building up a plurality of resin layers on a plaster cast comprising applying a first thin layer of a composition comprising a diurethanedimethacrylate prepared from 2,2,4-trimethylhexamethylenediisocyanate and 2-hydroxyethylmethacrylate, and a photopolymerization catalyst to the plaster cast and briefly exposing said thin layer to light whereby said thin layer is partially polymerized, successively applying at least one additional thin layer on said first thin layer and partially polymerizing each successive thin layer by brief exposure until the layer thickness and shape desired for the device or appliance are attained, and the shaped partially polymerized material is subsequently polymerized completely by exposure to light.

13 Claims, No Drawings

METHOD FOR PRODUCING ORTHODONTIC DEVICES AND APPLIANCES

This application is a continuation-in-part application of Ser. No. 697,776 filed Feb. 4, 1985 and now U.S. Pat. No. 4,568,558.

The invention relates to a method for producing orthodontic devices and appliances by the application of a material containing monomeric acrylates and/or methacrylates to a plaster cast and polymerizing the material.

BACKGROUND

Orthodontic devices and appliances are used to correct malocclusions and anomalies of tooth position.

If such devices and appliances are of arcylate- or methacrylate-based plastic, they can be produced by the application of powdered polyacrylate or polymethacrylate and a liquid monomer, typically methylmethacrylate, to plaster casts using the drip method or spraying or casting and by subsequent polymerization at an elevated temperature and under pressure.

Dental prostheses, orthodontic appliances and the like which comprise a plurality of plastic plates are well known, for example the process wherein they are shaped by deep drawing methods and disposed in several layers on top of one another, joined together by layers of adhesive, is described in German Utility Model No. DE-GM 6 753 339 (1968).

A method used in prosthodontics to produce tooth replacements is that of applying polymerizable material in layers to a plaster mold and polymerizing it by heating, exposing it to visible or ultraviolet light or some other means, (see for example German Patent DE-PS 1 516 456 and corresponding British Patent Specification No. 1,115,544 and German Patent Disclosure Document No. DE-OS 2 910 077 and corresponding U.S. Pat. No. 4,267,133).

THE INVENTION

It is the object of the invention to devise a method for producing orthodontic devices and appliances by the application of a polymerizable material to a plaster cast and polymerizing the material such as to enable the preparation of these devices and appliances with highly accurate detail, using a ready-to-use single-component material with practically unlimited workup time.

According to the invention, the method attaining this object provides that a material containing the diurethanedimethacrylate, which is prepared from 2,2,4-trimethylhexamethylenediisocyanate and 2-hydroxyethylmethacrylate, and a photopolymerization catalyst is applied to the plaster cast in a thin layer and is partially polymerized by brief exposure to light until it attains a gel-like consistency, this application in layers and exposure to light being repeated until such time as the layer thickness and shape desired for the device or appliance are attained, and that the partially polymerized material is subsequently polymerized completely by exposure to light.

The method according to the invention has proved to be particularly valuable if a material which contains not only at least 40% by weight, and preferably from 40 to 80% by weight, of the above-mentioned diurethanedimethacrylate but also a prepolymer based on an acrylated polyurethane or a prepolymer based on an acrylated epoxy resin and/or bis[4-(2-hydroxy-3-methacryloyloxypropoxyphenyl]-dimethylmethane (also known as bis-GMA) and one or more low-viscosity acrylates and/or methacrylates, also known as reactive diluents or diluent monomers.

All the known acrylates and methacrylates of this kind can be used as reactive diluents.

2-Hydroxyethylacrylate, tripropyleneglycoldiacrylate, pentaerythrittetraacrylate, butoxyethylacrylate, 2-hydroxyethylmethacrylate, butanedioldimethacrylate, triethyleneglycoldimethacrylate and dodecanedioldimethacrylate have proved to be particularly valuable.

By adding the prepolymers and/or the bis-GMA and the low-viscosity acrylates and methacrylates, a material is obtained which, because of its flow behavior, faithfully reproduces the surface of the cast, with its indentations and elevations, and tightly envelops clasps, wires, expansion screws and the like.

As a result of the first, brief exposure—approximately 5 to 10 seconds in duration—to light, the material which has been applied in layers and has a honey-like consistency is transformed into a layer that is capable of bearing weight and has a gel-like consistency, onto which further material can be applied without alteration of the partially polymerized material.

The accuracy of fit and the dimensional fidelity of the orthodontic devices and appliances produced using the method according to the invention are very good, because the surface of the cast is reproduced accurately, because of the transparency of the material, which enables accurate work, and because of the only slight change in volume (shrinkage due to polymerization) that takes place as a result of the layered structure and the partial polymerization.

Except for the clasps, wires, expansion screws and the like, the orthodontic devices and appliances produced by the method according to the invention are transparent and colorless—or, if a material colored with a suitable dye is used, they are colored.

The photopolymerization catalyst present in the material may be any known photoinitiator for the polymerization of acrylates and methacrylates.

Photoinitiators comprising ketones and reducing agents have proved valuable as disclosed, for example, in Pat. No. 4,071,424. Preferred photoinitiators are mixtures of camphor quinone and amines, such as methyldiethanolamine or triethanolamine, and particularly those which additionally contain benzoyl compounds known as photopolymerization catalysts, such as benzil acetals and benzoyl alkanols.

The exposure to light for the partial and for the complete polymerization can be effected with a halogen lamp of sufficient power available on the market, such as the tungsten-halogen lamp made by the Kulzer company, an ultraviolet emitter, such as a mercury vapor high-pressure lamp, or a mercury-vapor low-pressure lamp perhaps containing a luminous substance. or with a lamp that emits both visible and ultraviolet light.

In practice, it has proved valuable to use a fluorescent lamp with light having a wavelength of 340–380 nm or with light having a wavelength of 400–450 nm for the partial polymerization up to the gel-like consistency, and to use a lamp, such as the Dentacolor XS unit made by the Kulzer company, which emits light having a wavelength of 320–500 nm, that is, visible light plus ultraviolet light, for the complete polymerization.

The invention will be better understood from the ensuing detailed description of the production of an orthodontic device according to the method of the invention which has proven in practice to be particularly valuable, and of the material used therefor, which is preferably packed in non-transparent screw extruders or syringes, all taken in conjunction with the following examples.

EXAMPLE 1

Production of an Orthodontic Device

Method A

The material is applied to the previously prepared, isolated plaster cast in a thin layer, the clasps and wires used being carefully and thoroughly rinsed. The material is then partially polymerized by a brief exposure (5–10 sec) to light having a wavelength of 400–50 nm, in the course of which it attains a gel-like consistency. Further material is then added gradually in sequential layers and each such layer is partially polymerized by brief exposure to light (400–500 nm). Once the shape and character of the desired device is attained, the partially polymerized material located on the plaster cast is exposed for 2 minutes, and then for 1 minute more, after being removed from the plaster cast, to light having a wavelength of 320–500 nm to fully polymerize the resin material. The orthodontic device produced in this manner can then be further processed or handled in the usual manner, should this be necessary.

Method B

The production of the orthodontic appliance is carried out in accordance with Method A; however, light having a wavelength of 350–380 nm is used for the partial polymerization, and light having a wavelength of 320–500 nm is used for the complete polymerization.

Method C

The production of the orthodontic appliance is effected in accordance with Method A; however, light having a wavelength of 400–450 nm is used for the partial polymerization, and light having a wavelength of 350 nm (maximum intensity) is used for the complete polymerization.

EXAMPLE 2

Polymerizable Material (A)

40% by weight of diurethanedimethacrylate, produced from 1 mole of 2,2,4-trimethylhexamethylenediisocyanate and 2 moles of 2-hydroxyethylmethacrylate 37.5% by weight of an acrylated epoxy resin prepolymer made by the Degussa company, Frankfurt, designated as VPS 1928

20% by weight of triethyleneglycoldimethacrylate 0.2% by weight of camphorquinone 0.5% by weight of 1,2-diphenyl-2,2-dimethoxyethanone 1% by weight of 1-(4-dodecylphenyl)-2-hydroxy-2-methylpropanone 0.8% by weight of triethanolamine (B)

60% by weight of diurethanedimethacrylate, produced from 1 mole of 2,2,4-trimethylhexamethylenediisocyanate and 2 moles of 2-hydroxyethylmethacrylate 17.5% by weight of an acrylated epoxy resin prepolymer made by the Degussa company, Frankfurt, designated as VPS 1940

10% by weight of bis-GMA 0.2% by weight of camphorquinone 0.5% by weight of 1,2-diphenyl-2,2-dimethoxyethanone 1% by weight of 1-(4-dodecylphenyl)-2-hydroxy-2-methylpropanone 0.8% by weight of triethanolamine (C)

75% by weight of diurethanedimethacrylate, produced from 1 mole of 2,2,4-trimethylhexamethylenediisocyanate and 2 moles of 2-hydroxyethylmethacrylate 2.5% by weight of an acrylated epoxy resin prepolymer made by the Degussa company, Frankfurt, designated as VPS 1940

5% by weight of bis-GMA

5% by weight of pentaerythrittetraacrylate

10% by weight of triethyleneglycoldimethacrylate 0.2% by weight of camphorquinone 0.5% by weight of 1,2-diphenyl-2,2-dimethoxyethanone 1% by weight of 1-(4-dodecylphenyl)-2-hydroxy-2-methylpropanone 0.8% by weight of triethanolamine (D)

70% by weight of diurethanedimethacrylate, produced from 1 mole of 2,2,4-trimethylhexamethylenediisocyanate and 2 moles of 2-hydroxyethylmethacrylate 12.5% by weight of an acrylated polyurethane prepolymer made by the Degussa company, Frankfurt, designated as VPS 1748

5% by weight of bis-GMA

10% by weight of triethyleneglycoldimethacrylate 0.5% by weight of camphorquinone 1% by weight of 1-(4-dodecylphenyl)-2-hydroxy-2-methyldpropanone 1% by weight of tripropanolamine (E)

80% by weight of diurethanedimethacrylate, produced from 1 mole of 2,2,4-trimethylhexamethylenediisocyanate and 2 moles of 2-hydroxyethylmethacrylate 7.48% by weight of bis-GMA 10% by weight of dodecanedioldimethacrylate 0.02% by weight of macrolex red made by the Bayer company, Leverkusen 0.2% by weight of camphorquinone 0.5% by weight of 1,2-diphenyl-2,2-dimethoxyethanone 1% by weight of 1-(4-dodecylphenyl)-2-hydroxy-2-methylpropanone 0.8% by weight of triethanolamine The composition which is applied and first partially and then completely polymerized preferably contains from 40% by weight to 80% of the diurethanedimethacrylate; between 0% and 50% (and more preferably between 2.5% and 40%) of the prepolymer; and between 5% and 30% (and more preferably between 10% and 20%) of the low-viscosity acrylates and/or methacrylates.

The photopolymerization catalyst is preferably present in an amount between 0.5% and 10% and more preferably in an amount between 1% and 5%.

Each successive layer which is applied is partially polymerized sufficiently so that it has a gel-like consistency and retains its shape so that subsequent successfully applied layers can be applied thereon. This partial polymerization is readily attained with a brief exposure, for example, 5 to 10 seconds to light of a wavelength of 400–450 nm applied from the tungsten-halogen Tran-slux lamp.

The exposure time can be varied depending upon the radiation energy which depends on the power of the source and the distance of the radiation source.

The foregoing information is particularly applicable when the individual layers are applied to a thickness of between about 0.5 and 5 mm and preferably between about 0.5 and 3 mm.

We claim:

1. A method for producing orthodontic devices and appliances by building up a plurality of resin layers on a plaster cast comprising applying a first thin layer of a composition comprising a diurethanedimethacrylate prepared from 2,2,4-trimethylhexamethylenediisocyanate and 2-hydroxyethylmethacrylate, and a photopolymerization catalyst to the plaster cast and briefly exposing said thin layer to light whereby said thin layer is partially polymerized, successively applying at least one additional thin layer on said first thin layer and partially polymerizing each successive thin layer by brief exposure to light until the layer thickness and shape desired for the device or appliance are attained, and exposing said shaped partially polymerized material to light to completely polymerize said shaped material.

2. The method of claim 1, wherein said composition contains at least 40% by weight of said diurethanedimethacrylate.

3. The method of claim 2, wherein said composition also contains at least one prepolymer selected from the group consisting of acrylated polyurethane and acrylated epoxy resin, and/or bis-[4-(2-hydroxy-3-methacryloyloxypropoxy)phenyl]-dimethylmethane.

4. The method of claim 3, wherein said composition also contains at least one low-viscosity acrylate or methacrylate.

5. The method of claim 4, wherein said composition contains between 40% and 80% by weight of said diurethanedimethacrylate.

6. The method of claim 5, wherein the composition also contains, as the photopolymerization catalyst, a mixture of one or more ketones and an amine.

7. The method of claim 6, wherein said photopolymerization catalyst is a mixture of camphorquinone and an amine.

8. The method of claim 7, wherein said composition contains at least one low-viscosity acrylate or methacrylate selected from the group consisting of 2-hydroxyethylacrylate, tripropyleneglycoldiacrylate, pentaerythrittetraacrylate, butoxyethylacrylate, 2-hydroxyethylmethacrylate, butanedioldimethacrylate, triethyleneglycoldimethacrylate and dodecanediolmethacrylate.

9. The method of claim 1, wherein said composition comprises from 40% to 80% by weight of said diurethanedimethacrylate, from 0 to 50% of a prepolymer, between 5% and 30% of a low viscosity acrylate or methacrylate and from 0.5% to 10% of a photopolymerization catalyst.

10. The composition of claim 5 which contains between 2.5% and 40% of the prepolymer, between 5% and 30% of the low viscosity acrylate or methacrylate and between 1% and 5% of the photopolymerization catalyst.

11. The method of claim 10, wherein the composition also contains, as the photopolymerization catalyst, a mixture of one or more ketones and an amine.

12. The method of claim 10, wherein said photopolymerization catalyst is a mixture of camphorquinone and an amine.

13. The method of claim 12, wherein said composition contains at least one low-viscosity acrylate or methacrylate selected from the group consisting of 2-hydroxyethylacrylate, tripropyleneglycoldiacrylate, pentaerythrittetraacrylate, butoxyethylacrylate, 2-hydroxyethylmethacrylate, butanedioldimethacrylate, triethyleneglycoldimethacrylate and dodecanediolmethacrylates.

* * * * *